United States Patent [19]
Wolfinbarger, Jr. et al.

[11] Patent Number: 5,977,432
[45] Date of Patent: Nov. 2, 1999

[54] PROCESS FOR CLEANING BONE GRAFTS USING CENTRIFUGAL FORCE AND BONE GRAFTS PRODUCED THEREBY

[75] Inventors: Lloyd Wolfinbarger, Jr., Norfolk; Louis Ford, Virginia Beach, both of Va.

[73] Assignee: Life Net Research Foundation, Virginia Beach, Va.

[21] Appl. No.: 08/871,601

[22] Filed: Jun. 9, 1997

[51] Int. Cl.⁶ .................................................. A61M 31/100
[52] U.S. Cl. .............................. 623/16; 623/18; 128/898
[58] Field of Search ..................... 623/16, 18; 128/898; 134/33

[56] References Cited

U.S. PATENT DOCUMENTS

| | | | |
|---|---|---|---|
| 3,841,909 | 10/1974 | Nonaka et al. | 134/33 |
| 5,333,626 | 8/1994 | Morse et al. | 128/898 |
| 5,513,662 | 5/1996 | Morse et al. | 128/898 |
| 5,591,398 | 1/1997 | Knaepler et al. | 422/38 |
| 5,725,579 | 3/1998 | Fages et al. | 623/16 |
| 5,779,815 | 7/1998 | Breidohr et al. | 134/33 |
| 5,782,915 | 7/1998 | Stone | 623/11 |
| 5,797,871 | 8/1998 | Wolfinbarger, Jr. | 623/16 |
| 5,820,581 | 10/1998 | Wolfinbarger, Jr. | 623/16 |

*Primary Examiner*—Mickey Yu
*Assistant Examiner*—Suzette J. Jackson
*Attorney, Agent, or Firm*—Susanne M Hopkins

[57] ABSTRACT

A process for removing essentially all bone marrow from a cut bone graft and the cut bone graft produced thereby. A large substantially intact bone is selected and excess cartilage and associated soft tissues are removed from the surface of the bone. The bone is left whole or may be cut into appropriate smaller pieces constituting cut grafts and bone marrow is removed from the cancellous bone spaces of the small cut grafts through the application of centrifugal force. Prior to and/or following the application of centrifugal force, the bone graft may optionally be pretreated with one or more decontaminating agents, and/or solubilizing agents.

67 Claims, 4 Drawing Sheets

PROCESS FOR CLEANING BONE GRAFTS USING CENTRIFUGAL FORCE AND BONE GRAFTS PRODUCED THEREBY

FIELD OF THE INVENTION

The present invention is directed to a process for cleaning bone grafts including cut bone grafts using centrifugal force, and to bone grafts produced thereby.

BACKGROUND OF THE INVENTION

Human bone obtained from cadaveric donors is typically procured under sterile conditions in an operating suite environment of local hospitals. The bone is stored frozen until it is further processed into small grafts under similar sterile conditions, or under clean-room conditions.

Procurement and processing of human tissues is typically performed by groups certified by the American Association of Tissue Banks under standard operating procedures for the processing of each specific bone graft. Large bones such as the femur are thawed and debrided of excess tissue prior to being cut into smaller grafts.

Prior art methods of processing smaller grafts include cleaning of bone marrow from the cancellous bone spaces using mechanical means as disclosed in U.S. Pat. No. 5,333,626, including soaking, agitation, and/or lavage with pulsatile water flow under pressure. Cleaning may involve reduced or elevated temperatures, for example 4° C. to 65° C., and may also include the use of detergents or decontaminating agents. Typically, pulsatile water flow under pressure, even with the use of detergents or alcohols, only permits removal of that bone marrow which is accessible by the pulsatile flow of water, i.e. the immediate surface part of the cut bone graft.

U.S. Pat. No. 5,513,662 discloses cleaning large bone grafts, for example, a proximal femur, by subjecting the femur itself to a negative pressure gas atmosphere. 662' claims that the graft is cleaned due to leakage of the bone marrow elements and lipids, such leakage induced by placing the cut bone graft with or without holes drilled into the graft, in a bell jar and drawing a vacuum.

Although current donor screening protocols have been suggested to reduce the potential for transmission of the HIV virus through allograft tissues to less than one chance in from 1 to 10 million, the post procurement processing of allograft tissues is currently a manual process involving individual technician handling of the tissues. Since bone marrow represents the largest potential reservoir for any HIV virus present in an allograft bone tissue, it is expected that the process step of removal of bone marrow from the allograft bone tissues poses the greatest risk of transmission to the technician doing the processing. For example, a human femur may provide individual bone grafts consisting of portions of the bone shaft, femur head, proximal and/or distal femur grafts, and dividing the femur into these parts prior to removal of bone marrow increases the potential for process associated scattering of bone marrow elements within the processing room.

Bone marrow elements include hematopoietic progenitor cells, i.e., those stem cells that will ultimately differentiate into red blood cells, white blood cells, and platelets, among others. These stem cells are rich in major histocompatibility antigens (i.e., MHC antigens) that function in immune responses. Current processing techniques do not effectively remove bone marrow from the less solvent-accessible cancellous bone spaces within bone grafts, such as, for example, the trochanter portion or the femoral head area of the proximal femur, because current processing techniques rely upon soaking procedures which may or may not include agitation.

Typically, hydrogen peroxide is used to oxidize the colored elements within the bone marrow, which results in a cleaner appearance. However, such bone often still contains bone marrow which is extremely inmunogenic.

Further, most bone grafts are currently stored in the freeze-dried state. Freeze-drying removes water from the grafts, but lipid elements present in the membranes of the bone marrow cells and in vesicles present in adipocytes (i.e., fat storage cells) typically leak from the grafts after being placed in their final storage and distribution containers. Thus, these residues often give the appearance that the graft itself is not clean.

Cleaning of bone marrow from small bone grafts has been described in the scientific literature and in brochures and documents made public by groups involved in the procurement and processing of human tissues. A for-profit public corporation, Cryolife, Inc. (Marietta, Ga.) promotes a bone cleaning process designated as VIP™ (Viral Inactivation Process) and claims that the process provides "Cleaner bone through mechanical removal of debris and tissue such as bone marrow, lipids and blood components" and "Safer bone through inactivation of pathogens such as HBV and HIV (greater than 5-log kill) as well as bacteria and fungi" (Cryolife Orthopedics, Inc. brochure Feb. 12, 1992; Cryolife literature directed to Organ and Tissue Procurement Program Directors dated Feb. 20, 1992).

A second, for-profit publicly held corporation, Osteotech, Inc., Shrewsbury, N.J., describes a bone graft cleaning process called Permein™ ("a combination of ethanol and non-ionic detergent"; Mellonig, J. T., Prewett, A. B., and Moyer, M. P. J. Periodontol. December 1992, vol. 63, pp 979–983). This process involves the use of a solution of ethanol and detergent to clean bone grafts. Details of the process and detergents utilized are not currently available. Bone is soaked in the solution and it is claimed that the combination of ethanol and detergent facilitates permeation of the solution into bone. The process has been demonstrated to clean small cut-bone grafts and to be capable of inactivating the HIV in bone allograft (finely ground bone) (Mellonig, Prewett, and Moyer, J. Periodontology, December, 1992, 63: 979–983).

U.S. Pat. No. 5,556,379 describes a process for removing substantially all bone marrow from a large essentially intact bone using a vacuum mediated flow of solvent into the bone via the natural foramen and cartilaginous ends. This patent is directed primarily at the cleaning of bone marrow from large bones prior to their being cut into small cut bone grafts. U.S. Continuation-in-Part patent application Ser. No. 08/620,856 describes a composition for cleaning bone, U.S. Continuation-in-Part application Ser. No. 08/619,412 describes a process for cleaning large essentially intact bone grafts whereby a combination of positive and negative pressure is used to remove bone marrow from essentially intact bones prior to their being processed into cut bone grafts, U.S. Continuation-in-Part application Ser. No. 08/646,519 describes the use of ultrasonic cavitation in the cleaning of large essentially intact bone prior to their being processed into small cut bone grafts and for cleaning of small cut bone grafts, and U.S. Continuation-in-Part application Ser. No. 08/646,520 describes a recirculation method of cleaning large essentially intact bone prior to their being processed into smaller cut bone grafts. All of these patents and continuation in part patent applications are hereby incorporated in their entirety in this patent application.

The presently claimed process differs from prior art processes, including those disclosed in U.S. Pat. Nos. 5,333,626 and 5,513,662, in that the present process uses centrifugal force to remove bone marrow elements from the bone graft. The bone marrow elements are impelled outward from the bone graft from a center of rotation. Neither a "high pressure washing condition" as disclosed in U.S. Pat. No. 5,333,626 nor exposure of the graft to a negative pressure gas atmosphere, is used.

BRIEF DESCRIPTION OF THE DRAWINGS

The present invention is further explained in the description which follows with reference to the drawings, illustrating, by way of non-limiting examples, various embodiments of the invention, with like reference numerals representing similar parts throughout the several views, and wherein:

FIG. 1 is a side view of the custom centrifuge bottle capable of holding a bone graft during centrifugation. The specific dimensions below are preferable for a bottle capable of being used to clean, for example, a femur head. Specifically, the bottle includes a main vessel 2 having a preferred height of 12 cm and a preferred diameter of about 7.5 cm and a lid 1 which may be a snap on lid, pressure fitted lid, screw top lid or clamped on lid, preferably a snap top lid having a preferred height of about 1.5 cm, and a preferred diameter of about 8.0 cm. The lid 1 also includes a bore hole 3 for allowing access for an in line filter. The bottle preferably has a volume of about 750 ml. The bottle and lid can be composed of any material capable of withstanding any steps induced by centrifugation and being stable in the presence of any solution used in an embodiment of the present process, including plastics, polymers, composites and metals.

FIG. 2 is a top view of the custom centrifuge bottle capable of holding a bone graft during centrifugation having lid 1 and bore hole 3. Optional filter 4 is a commercially available filter to be inserted into hole 3 of lid 1 to allow for sterility and minimize pressure build-up.

FIG. 3 illustrates lid 1 having filter 4 inserted into bore hole 3.

FIG. 4 illustrates a side view of a holding device 5 designed to hold, for example, a whole femur head. The holding device is designed to fit into a custom centrifuge bottles as shown, for example in FIG. 1. The holding device 5 includes a disk 6 having a large bore hole 7 through its center and a plurality of small bore holes 8, preferably three bore holes 8. Inserted into bore holes 8 are support rods 9 to hold disk 6 in place after device 5 is placed into the bottle. The femoral or humeral head 11 is placed over large bore hole 7 and held in place with set screws 10 so that the graft is held in place while submerged. The holding device 5 served to hold the femoral/humeral head upright or upside down during processing and keeps the graft out of the bone marrow. The device 5 preferably has a height of about 12.0 cm and a diameter of about 7.5 cm.

FIG. 5 illustrates a side view of a holding device 12 designed to hold a cut bone graft 13, for example, a whole iliac crest wedge. The holding device 12 is designed to fit into a custom centrifuge bottles as shown, for example, in FIG. 1. The holding device 12 includes first primary disk 14a having a plurality of small bore holes 15 and a plurality (about three) of bore holes 16 having inserted there through a plurality of support rods 17. Disposed on the surface of first primary disk 14a is first disk 18a being porous and pliant and composed of, for example, foam, rubber or other polymeric materials, preferably foam. The graft 13 to be cleaned is disposed between first disk 18 and a second disk 18. Disposed on the second disk 18 is second disk 14. The graft 13 and disks 18a and 18, where the graft 13 is disposed between the first disk 18a and the second disk 18, are sandwiched between first and second primary disks 14a and 14, composed of, for example, metal, including steel, titanium, aluminum, etc. or a polymeric compound, Teflon, plastic, preferably metal. The primary disks 14a and 14 are held together via support rods 17 and set screws 19.

SUMMARY OF THE INVENTION

Figure 1:
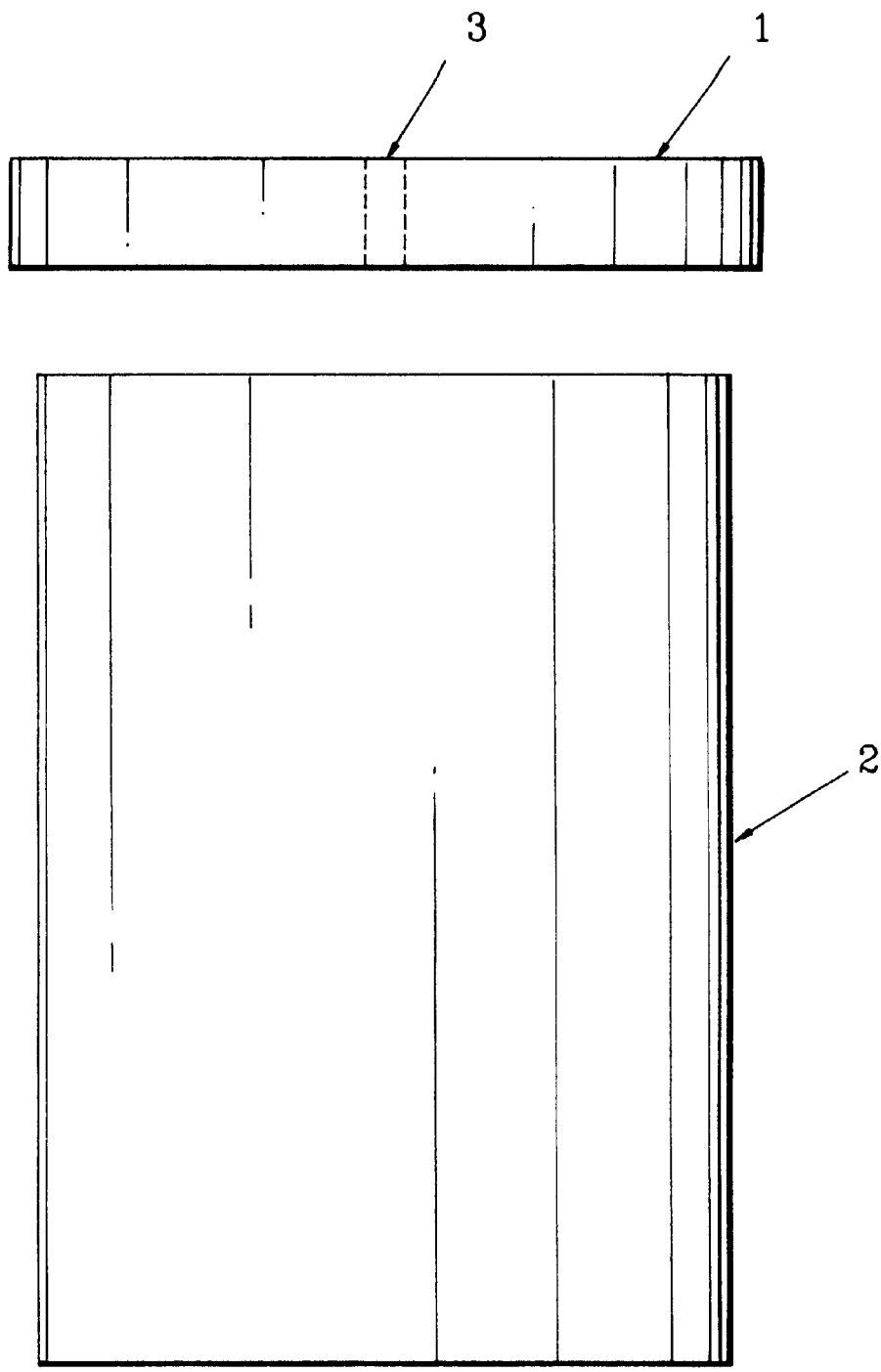
FIG. 1.
Figure 2:
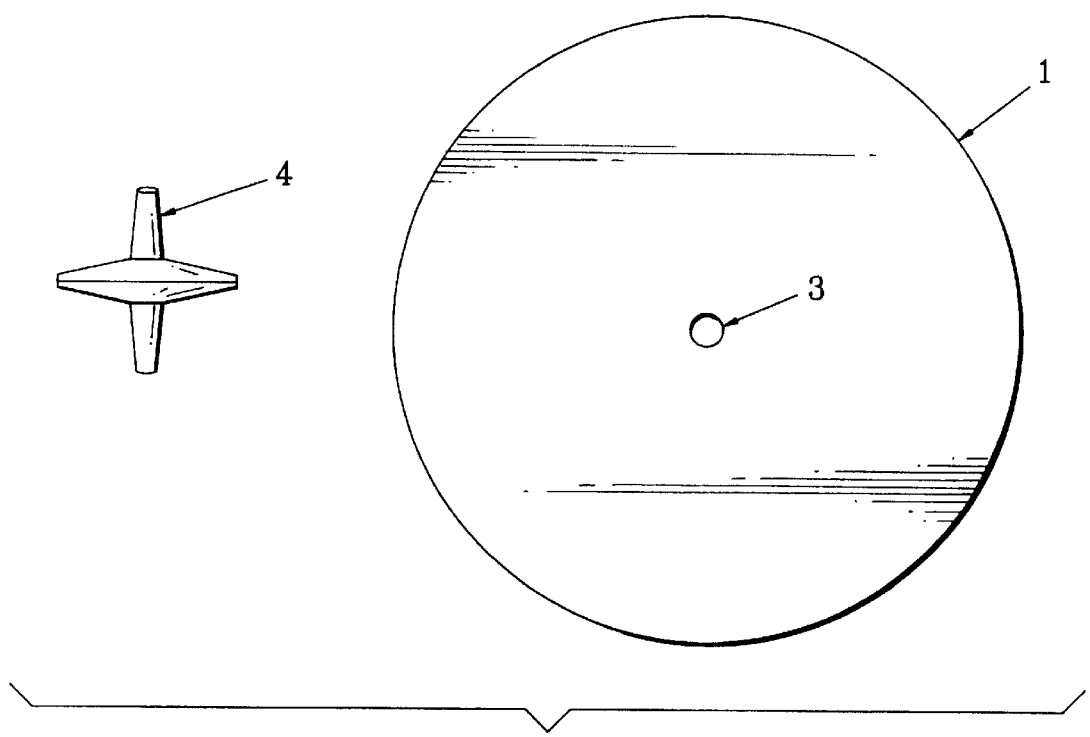
FIG. 2.
Figure 3:
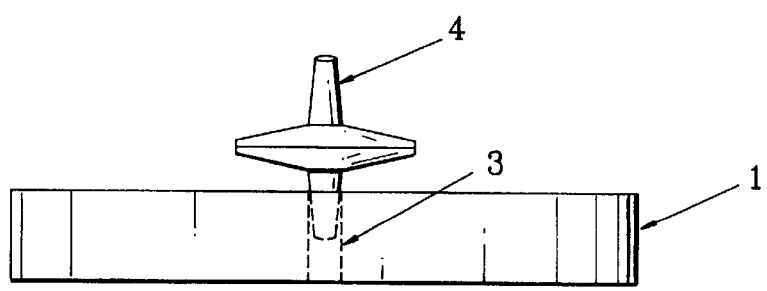
FIG. 3.

This invention relates to a process for the cleaning of bone grafts and bone grafts produced thereby including cut bone grafts suitable for transplantation into a human. The process is directed especially to human cadaveric bones, but is equally applicable to large bones obtained from other species.

The process involves the removal of bone marrow from the interstitial lumen and cancellous bone space by causing a flow of bone marrow from the cancellous bone space through creation of a centrifugational force. The bone marrow can be partially solubilized and dislodged from the cancellous bone space by use of amphiphilic solutes in a solvent with and without use of ultrasonic cavitation or the use of ultrasonic cavitation with or without the use of amphiphilic solutes. The solvent includes a combination of solutes which improve solvent penetration into and through the bone graft and intensifies cavitation induced by ultrasonics all of which act to increase the solubility of bone marrow, facilitating its removal from the cut bone graft by centrifugational force.

An object of the present invention is to provide a method and apparatus for removing bone marrow from the luminal and cancellous bone spaces of cut bone grafts including large and small cut bone grafts using centrifugal force.

An object of the present invention is to provide large and small cut bone grafts which are essentially free of residual bone marrow, for use in the preparation of bone grafts including small cut bone grafts, to be used in clinical applications. Large, essentially whole, bone grafts and small cut bone grafts without residual bone marrow offer additional advantages in that the removal of bone marrow, which may harbor potential viral particles and/or viral genomes integrated into the genomes of specific cell types present in the bone marrow, reduces the potential for transmission of infective agents such as bacteria and viruses, especially the human immunodeficiency virus (HIV), since cells capable of harboring the HIV virus are abundant in bone marrow. The removal of bone marrow from large, substantially intact, bone grafts and cut bone grafts including small cut bone grafts, also reduces the bioburden of viruses which may be present within the bone marrow cells removed.

Another object of the present invention is to provide cleaning procedures which remove substantially all of the bone marrow from cut bone grafts with minimal handling and processing, to reduce the risk of viral, bacterial and fungal transmission. The bone cleaning procedure according to the present invention results in the effective removal of substantially all of the bone marrow elements within the cancellous bone spaces of bone grafts.

Another object of this invention is the use of one or more solutions including, for example: alcoholic solutions (for example, ethanol, isopropanol and n-propanol) soluble amphiphile (i.e., detergent) solutions, antibiotic solutions, antiviral solutions, and hydrogen peroxide solutions in the removal of bone marrow from bone grafts. Alcohols and detergents have been demonstrated to be viricidal towards enveloped viruses including, for example, HIV, hepatitis, and herpes viruses. Further viruses which have been killed by compositions used in the instant invention include, for example, measles virus, togavirus, enterovirus, rhinovirus, rubella virus, reovirus, respiratory syncytial virus, cytomegalovirus, Epstein Barr Virus, Vesicular Stomatitis Virus, vaccinia virus, rabies virus, influenza virus, parainfluenza virus, adeno-associated virus, lymphoma virus, human papovirus, and lymphocytic choriomeningitis virus. Alcohols and detergents have been demonstrated to be bacteriocidal toward certain bacteria, including, for example, gonorrhea; gram negative bacteria including, for example, Yersinia enterocolitica; gram positive bacteria, including, for example, Myobacterium tuberculosis and Chlamydia, as well as acid fast bacteria.

Another object of the present invention is a holding device for holding a femoral or humeral head during processing.

Another object of the present invention is a holding device for holding a cut bone graft, for example, an iliac crest wedge.

Alcohol and detergent solutions also offer advantages of enhancing solubilization of bone marrow, reducing surface tension properties of aqueous solutions, and inactivating viruses and bacteria.

A further object of this invention is to provide methods for removing bone marrow from large and small cut bone grafts prior to their being further processed into clinically usable bone grafts. Thus, the present invention provides a process for cleaning small cut bone grafts which includes selecting a substantially intact bone, and cutting the bone into smaller cut bone grafts at which time centrifugational force is used to remove the bone marrow from the cancellous bone marrow spaces of large and small cut bone grafts.

An object of the present invention is to provide a cut bone graft essentially free from bone marrow.

A further object of the present invention is to provide a cut bone graft essentially free from viral and/or bacterial and/or fungal contamination.

Use of hypotonic solutions induces bone marrow cell swelling and subsequent lysis. Detergents and alcohols enhance rupture of the already swollen cells, with subsequent loss of cytoplasmic materials, and fragmentation and solubilization of cells.

DETAILED DESCRIPTION OF THE PREFERRED EMBODIMENTS

I. Definitions

Allowash™ Solution. By the term "Allowash™ solution" is intended those detergent compositions disclosed in co-pending U.S. patent application Ser. No. 08/620,856 incorporated herein by reference. Examples of suitable Allowash™ compositions include: a cleaning composition containing essentially about 0.06 wt % polyoxyethylene-4-lauryl ether, about 0.02 wt % poly (ethylene glycol)-p-nonyl-phenyl-ether; about 0.02 wt % octylphenol-ethyleneoxide and endotoxin free deionized/distilled water.

Amphiphile. By the term "amphiphile" is intended a detergent or wetting agent which contains groups that have both hydrophillic and hydrophobic properties.

Bone. By the term "bone" is intended for the purposes of the present invention any bone from any source, preferably human cadaveric bone.

Bone Marrow or Bone Marrow Elements. By the term "bone marrow elements" is intended for the purpose of the present invention the highly cellular hematopoietic connective tissue filling the medullary cavities and spongy epiphyses of bones which may harbor bacterial and/or viral particles and/or fungal particles, and includes, for example blood and lipid.

Centrifugational Force. For purposes of the present application, centrifugational force is calculated as relative centrifugational force (RCF) (normally expressed as "times gravitational force" or "X g", based on the general formula $RCF=1.12r(RPM/1000)^2$). By the term "centrifugational force" is defined as the force that tends to impel a thing or parts of a things outward from a center of rotation.

Cleaning Solution. By the term "cleaning solution" is intended for the purposes of the present invention, a liquid cleaning composition capable of at least one of the following: facilitating the solubilization of lipid, facilitating bone marrow removal, inactivating vim and/or bacterial particles, and/or disrupting cell membranes, which may contain, but is not limited to, one or more of the following: sterile water; saline; a detergent; a decontaminating agent; an acid; an alcohol, for example, ethanol and/or isopropanol; a combination of solutes desired to facilitate solubilization of bone marrow, for example, Allowash™ solution disclosed in co-pending application Ser. No. 08/620,856 herein incorporated by a reference; a chelating agent; a bacteriocidal agent; an antimycotic agent; an antiviral agent; sodium hydroxide or similar strong base; organic and/or inorganic acids including, for example, hydrochloric acid; and hydrogen peroxide. Lipophilic solvents include, for example, ethanol and chloroform.

Cut Bone Graft. As used herein, a "cut" bone graft is defined as one which is a part of a whole bone including one which is a substantial part of a whole bone and which may or may not be easily recognizable as to its origin. Practically speaking, cut bone grafts, as defined herein may include the range of small pieces of whole bones down to pieces at least as large as a distal femur and as small as a femur head of a whole bone and possibly as small as a cubic millimeter piece of a bone. The process possesses the attributes of being usable on a large number of bone grafts, including but not limited to, cancellous blocks, cancellous cubes, Cloward dowels, crock dowels, femoral condyles, femoral heads, femoral rings, femur segments, fibula segments, fibular wedges, frozen acetabula, distal femurs, femur shafts, hemi-pelvi, humerus shafts, proximal femurs, proximal femurs with head, proximal humeri, proximal tibias, proximal tibia/plateaus, talus, tibia shafts, tibia wafers, humeral heads, iliac crest wedges, ilium strips, mandibles, Midas Rex dowels, ribs, tibial segments, and radius/ulna wedges prior to subsequent processing into specific grafts. The present process is directed to human cadaveric bone as well as to large bones obtained from other species.

Decontaminating Agent. By the term "decontaminating agent" is intended one or more agents which remove or inactivate/destroy any biohazardous material potentially present in the bone marrow of a bone graft, for example, such materials including but not Limited to: bacteria, virus, and/or fungi; with such decontaminating agents including, for example, but not limited to one or more of the following: an antibacterial agent; an antiviral agent; an antimycotic agent; an alcohol for example, methyl, ethyl, propyl, isopropyl, butyl, and/or t-butyl; sodium hydroxide; hydrogen peroxide; and/or any detergent.

Detergent. By the term "detergent" is intended any agent which through a surface action that depends on it possessing both hydrophilic and hydrophobic properties and/or exerts oil-dissolving (cleansing) and/or antibacterial and/or antiviral effects, and can include but is not limited to: anionic detergents, non-ionic, cationic detergents acridine derivatives, long-chain aliphatic bases or acids, etc. Detergents are amphiphile compounds which facilitate solubilization of relatively insoluble lipids present in, for example, bone marrow.

Essentially Free From. By the term "essentially free from" is intended a bone graft where the material removed (i.e., bone marrow, viral, fungal, and/or bacterial particles) from the bone graft is not detectable using detection means known in the art at the time of filing of this application.

Lipid. By the term "lipid" is intended the fat-soluble constituents of bone marrow, for example fatty acids, triacylglycerols, glycerides, and phospholipids.

Pre-Cleaning Solution. By the term "pre-cleaning solution" is intended one or more of the following: the cleaning solution as defined above, water, saline, alcohol and hydrogen peroxide, preferably water.

Substantially Intact Bone Graft. By the term "substantially intact bone graft" is intended for the purposes of the present invention any whole bone including, for example, the femur, tibia, ilia, humurous, radius, ulna, ribs, whole vertebrae, mandibular, and/or any bone which can be retrieved from a donor with minimal cutting of that bone, for example, one half of an ulna, a femur cut in half to yield a proximal half and a distal half and/or at least a substantial portion of a whole bone, for example, at least one-quarter of a whole bone.

Ultrasonic Cleaner. By the term "ultrasonic cleaner" is intended any ultrasonic cleaning device capable of operating at: from 20 KHz to 50 KHz, preferably from about 40 KHz to about 47 KHz, and includes, for example, Branson ultrasonic cleaner model nos.: 1210, 2210, 3210, 5210 and 8210; or any similar ultrasonic cleaner.

Washing Solution. By the term "washing solution" is intended a solution including one or more of the following: water; saline or decontaminating agent including hydrogen peroxide and an alcohol; and a detergent. Preferably, the washing solution includes hydrogen peroxide or an alcohol.

II.

A. General Process

The present process includes the step of centrifuging a cut bone graft at a force effective and for a time effective to remove bone marrow from the cancellous bone space of the cut bone graft. For example, the bone grafts can be centrifuged at 1,000 to 5,000 rpm, preferably 2,000 to 3,500 rpm and most preferably 2,700 rpm, for a time, for example of from 5 to 25 minutes, preferably 10 to 20 minutes, and most preferably for 15 minutes.

Prior to and/or after first centrifuging, the bone grafts may optionally be incubated in one or more pre-cleaning solutions, cleaning solutions and/or washing solutions. After a particular incubation, the bone grafts may optionally be centrifuged.

The steps of pre-cleaning, cleaning and incubating can include one or more of: lavaging, soaking, sonicating and agitating the cut bone grafts. Agitation can be performed using, for example, a gyrating shaker and/or a paint can shaker.

Detergents are amphiphile compounds which facilitate solubilization of relatively insoluble lipids present in, for example, bone marrow, yet at higher concentrations tend to form micellar structures (Helenius, A. and Simons, K. Solubilization of Membranes by Detergents, Biochim. Biophys. Acta 415 (1975) 29–79). The formation of micellar structures tends to limit the effective concentration range for detergent solutions, and thus, soaking of bone in a given volume of detergent solution may not be totally effective in that the absolute amount of detergent present is limited and if the amount of lipid material to be solubilized exceeds the solubilization capability of the detergent present, lipid solubilization will not be complete. By continually changing the detergent solution over time, it becomes possible to completely solubilize all solubilizable lipid present in a bone graft.

Centrifugational induced flow of solvent through the cancellous parts of the bone minimizes mechanical and/or structural damage to the cancellous bone by causing a slow flow rate of bone marrow and associated cellular materials through the trabecular bone space occupied by bone marrow. The containment of aspirated bone marrow/solvent is made possible by use of disposable containers for collection of the aspirate. In addition, it becomes possible to add strong viral/bacterial inactivators, such as sodium hypochlorite, for example, to the disposable collection containers to further inactivate potential pathogenic and/or biohazardous biomaterials.

The use of more traditional flushing procedures to remove bone marrow involves the use of pressurized flow of solution as a rapidly moving stream which dislodges bone marrow by impact of the solvent on the bone graft. Such procedures tend to generate aerosols of tissue and solvent which can be hazardous to processing personnel. The present invention virtually eliminates this hazard.

For those bone grafts which do not lend themselves to vacuum induced cleaning as described in U.S. Pat. No. 5,553,379, the present invention provides a convenient and reproducible method for the cleaning of bone marrow from the cancellous bone marrow space of large and small cut bone grafts. The present invention involves a pre-treatment of the small cut bone grafts with amphiphilic agents and/or ultrasonic cavitation to enhance penetration of the amphiphilic agents and to loosen the associated bone marrow from the cancellous bone spaces.

The pre-cleaning solution when employed includes water and optionally one or more of the following: a decontaminating agent including an alcohol and hydrogen peroxide; and a detergent. Most preferably, water is employed as the first pre-cleaning solution, followed by incubating in a second pre-cleaning solution, preferably hydrogen peroxide.

One or more cleaning solutions may be employed. The cleaning solution may include one or more of the following: water, saline, a detergent and a decontaminating agent, for example, including hydrogen peroxide and alcohol.

Preferably, the cleaning solution includes endotoxin-free deionized/distilled water and which may include at least one solvent selected from the group consisting of anionic detergents and non-ionic detergents. Optionally, the first cleaning solution may include an alcohol, such as ethanol or isopropanol. Preferably, when employed the solution includes at least one or more of the following solvents: polyoxyethylene alcohols, polyethylene glycol p-isooctylphenylethers, polyoxyethylene nonylphenol, and polyoxyethylene sorbitol esters. More preferably, the solution includes Allowash™ solution (as described in U.S. Continuation-in-Part patent application Ser. No. 08/620,856 of parent application Ser. No. 08/293,206, filed Aug. 19, 1994, now abandoned, and) available from LifeNet Research Foundation, 5809 Ward Court, Virginia Beach, Va. Allowash™ solution comprises a solution of three detergents, i.e., (1) Brij-35 (more specifically, polyoxyethylene-4-lauryl ether having the chemical formula $C_9H_{19}(OCH_2CH_2)_4OH$, (2) Nonidet P-40 having the chemical name octyphenol-ethyleneoxide and also referred to as Tergitol NP-40, and sometimes referred to as NP-40, and (3) Nonoxynol-9 having the chemical name poly(ethylene glycol)p-nonyl-phenyl-ether.

The detergent solution when employed preferably includes about 0.0001× to 10× of a 1× detergent solution containing about 0.066 wt % Brij-35, about 0.02 wt % Nonidet P-40, and about 0.02 wt % Nonoxynol-9 in endotoxin free water, preferably, about 0.001× to 0.1× of the 1× detergent solution, more preferably, about 0.001× to 0.01× of the 1× detergent solution, and, most preferably, about 0.005× to 0.01× of the 1× detergent solution.

The cleaning solution may optionally include one or more of the following: an antibiotic, an antiviral agent, an antiviral, an antimycotic agent, hydrogen peroxide, a permeation enhancer, an organic acid and a dilute solution of one or more strong acids.

Preferably, when employed a subsequent cleaning solution includes one or more of the following: about a 0.01× solution of the 1× detergent solution and hydrogen peroxide. The process can include refilling the container with the second cleaning solution for further processing the bone including flushing the first solution from the bone; and enhancing penetration of the second solution through the cancellous bone marrow space through the use of ultrasonic cavitation so that a maximum concentration of solution in the bone is equivalent to 0.1× to 0.01 × detergent solution.

Alcohol, may be optionally included in the cleaning solution at a concentration of about 5 to 95% alcohol, measured by a volume-to-volume ratio, more preferably in the range of about 10 to 30% alcohol, measured by a volume-to-volume ratio. Preferred alcohols are ethanol and isopropanol.

The concentration of detergent in the cleaning solution ranges from about 0.001 to 2 wt %, more preferably from about 0.01 to 0.5 wt %. Preferably, the first and/or second cleaning solution is controlled within a temperature range of about 20° C. to 65° C. and maintained within the temperature range during processing. More preferably, the temperature range is controlled and maintained at about 27° C. to 55° C. Even more preferably, the temperature range is controlled and maintained at about 37°0 C. to 44° C. Preferably, the container of solution which contains the bone is immersed into a temperature controlled water bath, for more stable temperature control.

Most preferably, at least one of the cleaning solutions employed includes Allowash™ solution, hydrogen peroxide and one or more antibiotics.

A washing solution when employed is used in the present process for flushing the cleaning solution from the bone and for further reducing bacterial, fungal or viral contaminants. The washing solution includes at least one of the following components: water, preferably endotoxin-free deionized/distilled; saline; a decontaminating agent, for example an alcohol, including, for example ethanol, and hydrogen peroxide; and a detergent. The washing solution may optionally include one or more of the following components: an antibiotic, an antiviral agent, a permeation enhancer, an organic acid and a dilute solution of one or more strong acids. One or more washing steps and/or solutions may be employed. Preferred washing solutions include alcohol and hydrogen peroxide.

The present invention also includes bone grafts produced by the process steps described above.

Initial bone marrow removal is preferably facilitated by agitation in a pre-cleaning solution, preferably in sterile endotoxin free deionized/distilled water. This hypotonic solution results in swelling of the cellular components of the bone marrow facilitating their subsequent disruption by amphiphilic agents. The vigorous agitation dislodges bone marrow from the approximate surface of the cut bone grafts further facilitating subsequent bone marrow removal upon immersion of the cut bone grafts into a container containing a cleaning solution of a sterile mixture of at least one detergent in endotoxin-free deionized/distilled water.

Detergents are typically evaluated based on their "critical micelle concentration" (CMC). The CMC is that concentration of detergent in solution where free molecules of detergent begin to aggregate into micellar structures. The concentration of detergent that is utilized in the cleaning solution preferably includes concentrations of at least one detergent that exceeds the CMC so that there is sufficient detergent available in the solution to have micelles present in the solution to replenish monomeric detergent as it is consumed in bone marrow solubilization.

Moreover, cleaning solutions used in the present invention are non-toxic and/or leave a non-toxic residual concentration of materials in the bone after flushing with a subsequent solution. In particular, following cleaning of bone grafts, it is necessary that residual detergents which may remain associated with the bone graft are not toxic towards human fibroblast cells expected to migrate into the bone graft material(s) following implantation.

In accordance with the present invention, solutions can comprise concentrations of about 0.0001× to 10×, preferably 0.001× to 0.1×, more preferably 0.001× to 0.01×, and most preferably 0.005× to 0.01×. As discussed above, these solutions should preferably be at a concentration so that upon completion of cleaning of the bone, e.g., prior to implantation, the concentration of detergents and/or any of materials in the solution is below a toxic level. For example, a 0.01× solution is a preferred solution, because removal of 90 percent of this solution from the bone, such as by subsequent flushing with secondary solutions, reduces the concentration to approximately a 0.001× solution, which is the non-toxic level. Thus, a 0.01× solution provides a highly cost effective solution having an effective concentration of detergents without wasting excess detergents.

Formulations including solutions of detergents of Brij-35, Nonidet P-40, and Nonoxynol-9 are disclosed in. U.S. Continuation-in-Part patent application Ser. No. 08/620,856, which discloses these formulations which may be used in combination with stabilizers so as to temporarily fix red blood cells thereby allowing sufficient time for the composition to inactivate viruses and bacteria while keeping red blood cells intact and undamaged. U.S. Continuation-in-Part patent application Ser. No. 08/620,856 is hereby incorporated by reference in its entirety for its disclosure concerning detergents that are effective in reducing or killing microorganisms and viruses in a relatively short period of time.

The cleaning solutions of the present invention can include any extraneous components in amounts that are not detrimental to the cleaning of the bone. For example, components that may be a detrimental contaminant at higher concentrations can be non-toxic and/or without consequence to the cleaning efficiency of the cleaning solution at lower concentrations. Thus, for example, stabilizers, including glutaraldehyde and sucrose as disclosed in U.S. patent application Ser. No. 08/212,698, can be included in the cleaning solution in amounts that would not be detrimental to the cleaning ability of the cleaning solution and in amounts that would be non-toxic in the bone graft to be implanted.

Methods of determining of the degree to which the bone marrow has been removed from the bone graft include:

monitoring by taking core samples of bone plugs, solubilizing bone marrow in the bone plug core samples using sodium hydroxide and taking a protein assay of the same; visual inspection of the trabecular bone can be examined using a scanning electron microscope; gross visual examination can be performed by cutting the graft open for visual inspection by the naked eye or with a stereoscope, for example, and absorbance of soaking solutions at 410 nm. Monitoring may be preformed at various intervals, for example: after pre-cleaning, continually during the process, at discreet times during the process, and/or after major process steps. For example, after it has been determined that a substantial amount of the bone marrow has been removed from the bone grafts (i.e., the bone graft) the bone grafts are removed from the solution and treated with a second solution. The bone is then immersed in the second solution in the container, for further processing. When it has been determined that a further substantial part of the bone marrow has been removed, the bone is then immersed in a subsequent solution in the container for further processing. Preferably, the first solution to be distributed through the bone graft may include endotoxin-free deionized/distilled water, alcoholic, e.g., ethanolic solutions of water, or isotonic saline in endotoxin-free deionized/distilled water. The second solution to be distributed through the bone graft may include a solution of amphiphilic agents in endotoxin-free deionized/distilled water, alcoholic, e.g. ethanolic solutions of water, or isotonic saline in endotoxin-free deionized water, alcoholic solutions. The third solution to be distributed through the bone graft may include hydrogen peroxide in sterile endotoxin-free deionized/distilled water. The fourth solution to be distributed through the bone graft may include 70% isopropyl alcohol with the fifth solution being endotoxin-free deionized/distilled water to remove residues of all processing reagents.

The second solution is distributed though the bone in order to reduce the amount of the first solution in the bone graft and/or to deliver additional agents to be used in processing of the bone graft. For example, addition of ethanol (50% to 100%, volume to volume) to the solution serves to reduce bacterial, fungal and/or viral contaminants which might be present in the bone graft. The use of absolute (100%) ethanol/isopropanol in the fourth solution would further serve to dehydrate the bone, reducing subsequent times needed for freeze-drying. Since the flow of solution through the bone graft will be less restricted during flushing with the second solution, the incubation times may be reduced.

Optionally, one or more of the following components may be added to any one of the pre-cleaning, cleaning, or washing solutions being used to clean and flush the bone graft, respectively, including, but not limited to: antibiotics, antiviral agents (for example, peroxide generating agents such as EXACT, e.g., trademarked haloperoxidase products marketed by ExOxEmis, Inc., San Antonio, Tex.), hydrogen peroxide, permeation enhancers (for example, fatty acid esters, such as laurate, myristate and stearate monoesters of polyethylene glycol), organic acids (for example, citric acid) or dilute solutions of strong acids (for example, hydrochloric acid).

B. A Preferred Embodiment of the Present Process

In a preferred embodiment, the present process for cleaning cut bone grafts, includes selecting a large substantially intact bone and cutting cut bone grafts using, for example, a band or Stryker® saw. Jagged edges are cut from the cancellous bone block which may have been left from the recovery procedures. The cut bone grafts are briefly pre-cleaned by, for example, rinsing with sterile water at a temperature of from about 20° C. to 65° C., preferably 27° C. to 55° C. and most preferably from 37° C. to 44° C.

The cut bone grafts are placed in a sterile can and again pre-cleaned with, for example, sterile water at a temperature of from about 20° C. to 65° C., preferably 27° C. to 55° C. and most preferably from 37° C. to 44° C. The can is agitated for a time period of at least 5 minutes, preferably for at least 12 minutes and most preferably for from 12 minutes to 30 minutes at from 300 to 700 rpms, preferably at about 500 rpms.

At this point the cut bone grafts may optionally be cleaned by placing into a basin of cleaning solution preferably containing, for example, an amphiphilic solution for at a time period of at least 5 minutes, preferably at least 15 minutes and most preferably from 15 minutes to 30 minutes and/or preferably into 3% hydrogen peroxide for a time period of at least 5 minutes, preferably at least 15 minutes and most preferably from 15 minutes to 30 minutes.

The cut bone grafts are then transferred in the hydrogen peroxide solution into their respective centrifuge tubes and centrifuged at from 1,000 to 5,000 rpm, preferably 2,000 to 3,500 rpm, and most preferably at approximately 2,500 (1657×g) rpm for from 5 to 25 minutes, preferably from 10 to 20 minutes, and most preferably for about 15 minutes. The bone grafts are then removed from their respective centrifuge tubes and again cleaned by, for example, adding to a sterile basin of an ultrasonic cleaner containing a cleaning solution preferably including, for example, a mixture of Allowash™ solution, hydrogen peroxide, and antibiotics and sonicated at a temperature of from 20° C. to 65° C., preferably 27° C. to 55° C., and most preferably 37° C. to 44° C. for a minimum of 15 minutes, preferably 1 hour.

The cut bone grafts are then washed, for example, using sonicating, by replacing the solution in the basin of the sonicator with hydrogen peroxide, preferably 3% hydrogen peroxide, and the grafts are sonicated for a minimum of one hour, preferably 90 minutes. The grafts are then incubated in a washing solution, preferably 1–3% hydrogen peroxide optimally 3%, for example, soaking for a time period of at least 6 hours, preferably about 6 to 24 hours, and more preferably about 8 to 14 hours (or overnight) at a temperature of from 20° C. to 65° C., preferably 27° C. to 55° C., and most preferably 37°–44° C.

The washing solution is then decanted and replaced with a new washing solution, including, for example, isopropyl alcohol preferably with 70% (volume to volume) alcohol. The grafts are incubated, for example, by soaking at room temperature for 30 minutes or less, preferably 15 minutes.

The washing solution is then decanted and replaced with warm sterile water, (This water wash may optionally contain one or more decontaminating agents.) preferably (37°–44° C.) and incubated for 30 minutes or less, preferably 5 minutes or less, more preferably 5 minutes. The grafts are then removed from the basin and placed into their respective centrifuge tubes. The grafts are then centrifuged at from 1,000 to 5,000 rpm, preferably 2,000 to 3,500 rpm, and most preferably about 2,500 rpm, for 30 minutes or less, preferably 15 minutes or less, more preferably 3 minutes. At this time the grafts are essentially free from bone marrow in the cancellous bone spaces and can be freeze-dried and packaged for distribution.

C. A Further Preferred Embodiment of the Present Process

A preferred process for cleaning cut bone grafts including small cut bone grafts according to the present invention includes selecting a large substantially intact bone and cutting appropriate small cut bone grafts using a band or Stryker® saw. Jagged edges are cut from the cancellous bone block which may have been left from the recovery procedures. The cut bone grafts are placed in a sterile can with sterile water at 37° C. to 44° C. The can is filled with sterile water and agitated for at least 12 minutes at 300 to 700 rpms. The cut bone grafts are then optionally placed into a basin containing amphiphilic solution for at least 15 minutes and/or into 3% hydrogen peroxide for at least 15 minutes. The cut bone grafts are then transferred into their respective centrifuge tubes and centrifuged in 3% hydrogen peroxide at approximately 2,500 rpm for 15 minutes. The bone grafts are then removed from their respective centrifuge tubes and added to the sterile basin of an ultrasonic cleaner containing a mixture of Allowash™ solution, hydrogen peroxide, and antibiotics and sonicated at 37° C. to 44° C. for a minimum of 1 hour. The solution in the basin of the sonicator is then replaced with 3% hydrogen peroxide and the grafts sonicated for a minimum of one hour at which time the grafts are incubated overnight at 37°–44° C. (or for a minimum of 90 minutes). The hydrogen peroxide solution is then decanted and replaced with 70% (volume to volume) isopropyl alcohol. The grafts are incubated at room temperature for a minimum of 15 minutes. The isopropyl alcohol is then decanted and replaced with warm sterile water (37°–44° C.) and incubated for a minimum of 5 minutes. The grafts are then removed from the basin of the sonicator and placed into their respective centrifuge tubes. The grafts are then centrifuged at 2,500 rpm for a minimum of 3 minutes. At this time the grafts are essentially free of bone marrow in the cancellous bone spaces and can be freeze-dried and packaged for distribution.

The produced grafts are essentially free from viral and/or bacterial contamination.

In a preferred embodiment, the present procedure for producing a cleaned bone graft includes the following: selecting a substantially intact bone; cutting the substantially intact bone into cut bone grafts; pre-cleaning the cut bone grafts in a pre-cleaning solution to produce pre-cleaned cut bone grafts; cleaning the pre-cleaned cut bone grafts in a cleaning solution to produce first cleaned cut bone grafts; centrifuging the first cleaned cut bone grafts to produce centrifuged cut bone grafts; washing the centrifuged cut bone grafts in a washing solution to produce washed cut bone grafts; incubating the washed cut bone grafts in water to produce incubated cut bone grafts; and centrifuging the incubated cut bone grafts to produce cleaned bone grafts suitable for transplantation into a human.

D. A Holding Device for Cleaning a Femoral or Humeral Head

Figure 4:
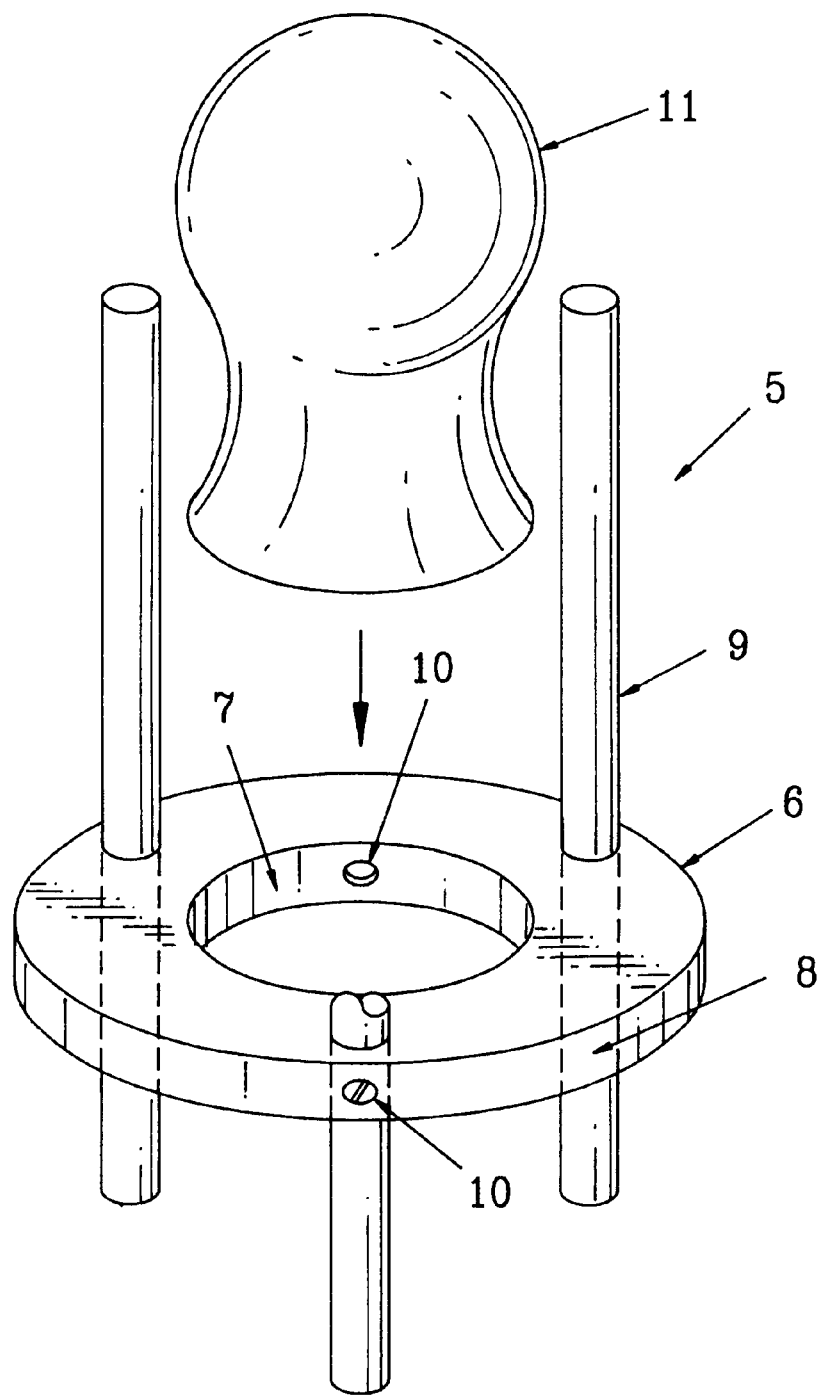
FIG. 4.

FIG. 4 illustrates a side view of a holding device 5 designed to hold a whole, for example, femur head. The holding device is designed to fit into a custom centrifuge bottles as shown, for example in FIG. 1. The holding device 5 includes a disk 6 having a large bore hole 7 through its center and a plurality of small bore holes 8, preferably three bore holes 8. Slidably inserted or frictionally fit into bore holes 8 are support rods 9 to hold disk 6 in place after device 5 is placed into the custom centrifuge bottle as shown in FIG. 1. The femoral or humeral head 11 is placed over large bore hole 7 and held in place with set screws 10 so that the graft is held in place while submerged. The holding device 5 served to hold the femoral/humeral head upright or upside down during processing and keeps the graft out of the bone marrow. The device 5 preferably has a height of about 12.0 cm and a diameter of about 7.5 cm. Disk 6, support rods 9 are composes of any material capable of withstanding any stress induced by centrifugation and being stable in the presence process.

Figure 5:
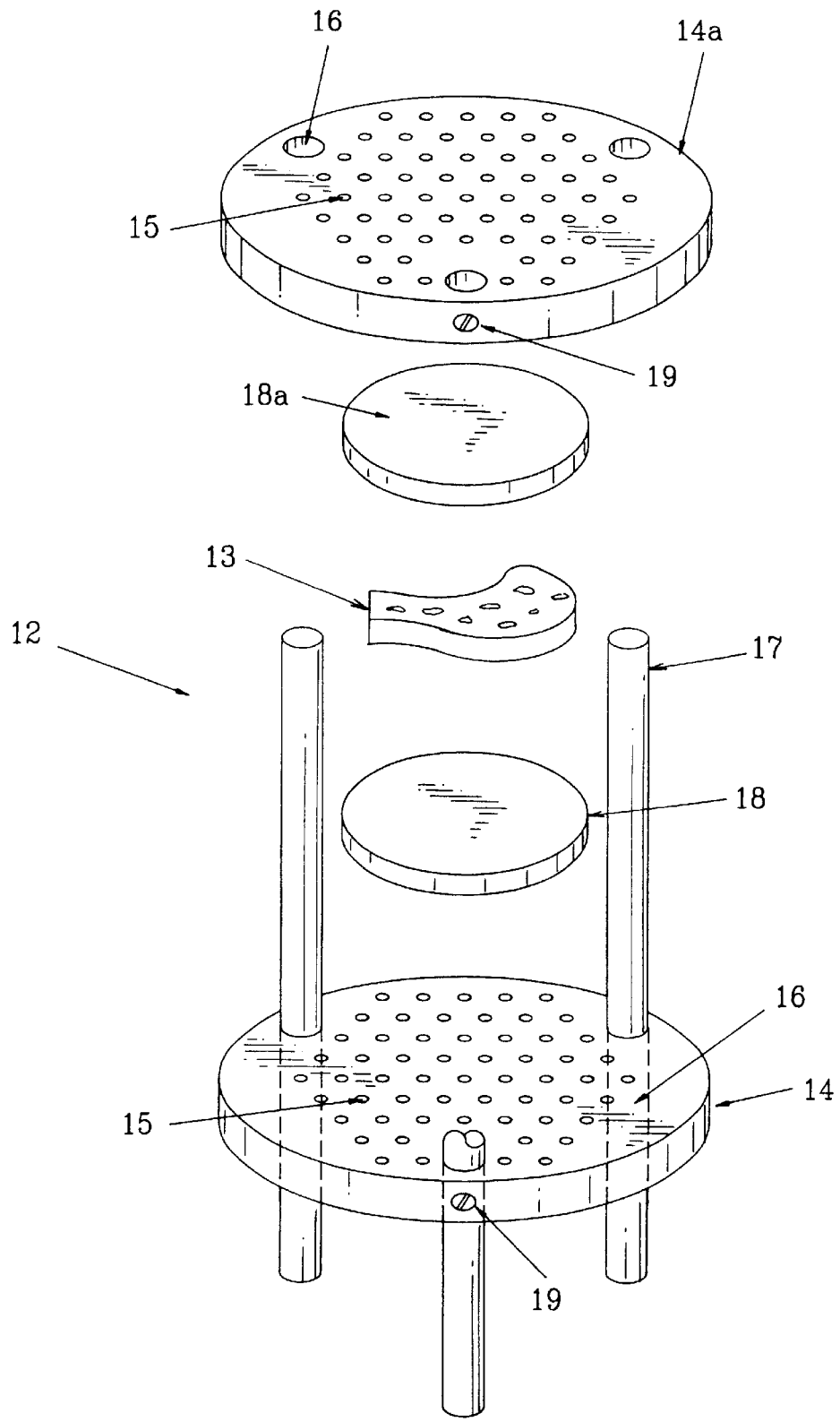
FIG. 5.

E. A Holding Device for Cleaning a Cut Bone Graft Including an Iliac Crest Wedge FIG. 5 illustrates a side view of a holding device 12 designed to hold a cut bone graft, for example, a whole, for example, iliac crest wedge 13. The holding device 12 is designed to fit into a custom centrifuge bottles as shown, for example, in FIG. 1. The holding device 12 includes first primary disk 14a having a plurality of small bore holes 25 and a plurality (preferably three) of bore holes 16 having inserted there through a plurality of slidably disposed or frictionally fit support rods 17. Disposed on the surface of first primary disk 14a is first disk 18a being porous and pliant composed of, for example, foam, rubber or other polymeric materials, preferably foam. The graft 13 to be cleaned is disposed between first disk 18a and a second disk 18 primary. Disposed on the second disk 18 is second disk 14. The disks and graft are sandwiched between first and second primary disks 14a and 14. First and second primary disks 14a and 14, and support rods 17 are composed of any material capable of withstanding any stress induced by centrifugation and being stable in the presence of the various solutions used in the present process, for example, metal, including steel, titanium, aluminum, etc. or a polymeric compound, Teflon, plastic, ceramics, and composites. Disks 14a and 14 are preferably metal. The disks 14 are held together via support rods 17 and set screws 19.

EXAMPLES

The following examples illustrate processing of bone grafts according to the instant invention.

Example 1

Process for Cleaning an Ilium

All soft-tissue and periosteum was removed from an ilium using periosteal elevators and sharp dissection. The ilium was placed securely in Pan-A-Vise™ with the iliac crest oriented superiorly or the ilium was held directly on the working surface. Sizes of iliac crest wedges (ICWs) to be fashioned were determined, based on the "thickness" of various sections of the iliac crest or processing instructions. ICWs were fashioned into appropriate sized grafts using a Stryker® saw with twin blade assembly. The blade spacing was adjusted with the Allen-headed set-screw. The ICWs were removed from the ilium by cutting the base of the grafts away from the remaining ilium using a Stryker® saw with single blade assembly. The base of the fashioned ICW was trimmed parallel with the top of the graft. The iliac crest wedge(s) were cleansed using the pulsatile water apparatus (Alternatively, the ICWs could be shaken or in a container with warm water (37°–44° C.)). The iliac crest wedge(s) were placed in a sterile container with hydrogen peroxide at 37° to 44° C. with care taken to avoid containment of the gas generating reaction. The container was closed and placed into centrifuge. The centrifuge was balanced. The grafts were centrifuged at 2,500 rpm for 15 minutes. The tissue was removed from the centrifuge and the grafts were placed into an ultrasonic cleaner. The ultrasonic cleaner contained a mixture of Allowash™ solution, hydrogen peroxide, and antibiotics. The grafts were sonicated at 37°–44° C. for 1 hour. The grafts were removed from the ultrasonic cleaner. The antibiotic mixture was decanted and the container was filled with fresh hydrogen peroxide. The top of the container was closed and the wedges were sonicated for 90 minutes. The sonicator was turned off, and the grafts were incubated overnight at 37°–44° C. (a minimum of 6 hours). The hydrogen peroxide was removed and the container refilled with 70% isopropyl alcohol. The grafts were incubated in 70% isopropyl alcohol at room temperature for a minimum of 15 minutes. The 70% isopropyl alcohol was decanted and the container was filled with warm (37°–44° C.) sterile water. The grafts were incubated for a minimum of 5 minutes. The sterile water was decanted and the iliac crest wedge(s) were removed from the container. The iliac crest wedge(s) were placed in a sterile container. The container was sealed and placed into the centrifuge. The centrifuge was balanced. The grafts were centrifuged for 3 minutes to dry and remove any remaining water. The width, length, and thickness of the iliac crest wedges were measured and each graft was assigned an identification number. The fashioned graft(s) were packaged as appropriate for the particular needs of distribution.

Example 2

Process for Cleaning a Proximal Femur

All soft-tissue and periosteum were removed from the proximal femur using periosteal elevators and sharp dissection. The femur was placed securely in Pan-A-Vise™ with the femur head oriented superiorly or the femur was held directly on the working surface. The femur was cut to fashion the femur head. The femur head was fashioned into the appropriate sized grafts using a Stryker® saw with single blade assembly. The femur head was removed from the proximal femur by cutting the base of the grafts away from the remaining proximal femur using a Stryker® saw with single blade assembly. The base of the fashioned femur head was trimmed parallel with the top of the graft. The femur head(s) was cleansed using the pulsatile water apparatus or the grafts was shaken in a container with warm water (37°–44° C.). The femur head(s) was placed in a sterile container with hydrogen peroxide at 37° to 44° C. with care to avoid containment of the gas generating reaction. The container was closed and placed into the centrifuge. The centrifuge was determined to be balanced. The graft(s) was centrifuged at 2,600 rpm for 15 minutes. The tissue was removed from the centrifuge and the grafts placed into an ultrasonic cleaner to the ultrasonic cleaner was added a mixture of Allowash™ solution, hydrogen peroxide, and antibiotics and the tissue was sonicated at 37°–44° C. for 1 hour. The tissue was removed from the ultrasonic cleaner. The antibiotic mixture was decanted and the container was filled with fresh hydrogen peroxide. The top was closed and the wedge(s) was sonicated from one hour. After the sonicator was turned off, the grafts were incubated overnight at 37°–44° C. (a minimum of 6 hours). The hydrogen peroxide was decanted and the container was filled with 70% isopropyl alcohol and the grafts were incubated at room temperature for a minimum of a 15 minutes. The 70% isopropyl alcohol was decanted and the container was filled with warm (37°–44° C.) sterile water. The grafts were incubated for a minimum of 5 minutes. The sterile water was decanted and the femur head(s) was removed from the container. The femur heads(s) were placed in a sterile container. The container was sealed and placed into the centrifuge. The centrifuge was determined to be balanced. The grafts were centrifuged for 3 minutes to dry and removed any remaining water. The diameter and the length of the grafts were measured and assigned graft identification numbers. The fashioned graft(s) were packaged as appropriate for the particular needs of distribution.

Example 3

Process for Cleaning a Proximal Femur

All soft-tissue and periosteum were removed from the proximal femur using periosteal elevators and sharp dissection. The femur was placed securely in Pan-A-Vise™ with the femur head oriented superiorly or the femur was held directly on the working surface. The femur was cut to fashion the femur head. The femur head was fashioned into the appropriate sized grafts using a Stryker® saw with single blade assembly. The femur head was removed from the proximal femur by cutting the base of the grafts away from the remaining proximal femur using a Stryker® saw with single blade assembly. The femur head was cut into small pieces of cancellous cubes and the cancellous cube(s) was cleansed using the pulsatile water apparatus or the grafts were shaken in a container with warm water (37°–44° C.). The cancellous cubes(s) was placed in a sterile container with hydrogen peroxide at 37° to 44° C. with care taken to avoid containment of the gas generating reaction. The container was sealed and placed into the centrifuge. The centrifuge was determined to be balanced. The grafts were centrifuged at 2,600 rpm for 15 minutes. The tissue was removed from the centrifuge and the grafts were placed into an ultrasonic cleaner to the ultrasonic cleaner was added a mixture of Allowash™ solution, hydrogen peroxide, and antibiotics and the tissue was sonicated at 37°–44° C. for 1 hour. The tissue was removed from the ultrasonic cleaner. The antibiotic mixture was decanted and the container was filled with fresh hydrogen peroxide. The top was closed and the wedges were sonicated from one hour. After the sonicator was turned off, the grafts were incubated overnight at 37°–44° C. (a minimum of 6 hours). The hydrogen peroxide was decanted and the container was filled with 70% isopropyl alcohol and the grafts were incubated at room temperature for a minimum of 15 minutes. The 70% isopropyl alcohol was decanted and the container was filled with warm (37°–44° C.) sterile water. The grafts were incubated for a minimum of 5 minutes. The sterile water was decanted and the cancellous cube(s) were removed from the container. The cancellous cube(s) were placed in a sterile container. The container was sealed and placed into the centrifuge. The centrifuge was balanced. The grafts were centrifuged for 3 minutes to dry and any remaining water was removed. The diameter and length of the graft were measured and assigned graft identification numbers. Place the fashioned graft(s) into the inner package and heat seal. The package was placed with the graft into the larger peelable bag labeled with the unique numeric designator and heat sealed. The foregoing was repeated until all cancellous cube grafts were packaged.

Example 4

Process for Cleaning a Proximal Tibia

All soft-tissue and periosteum were removed from the proximal tibia using periosteal elevators and sharp dissection. The tibia was placed securely in Pan-A-Vise™ with the tibia head oriented superiorly or the tibia was held directly on the working surface. The tibia was cut to fashion the tibia head. The tibia head was fashioned into the appropriate sized grafts using a Stryker® saw with single blade assembly. The tibia head was removed from the proximal tibia by cutting the base of the grafts away from the remaining proximal tibia using a Stryker® saw with single blade assembly. The tibia head was cleaned using the pulsatile water apparatus or the grafts were shaken in a container with warm water (37°–44° C.) and incubated. The tibia head was placed in a sterile container with hydrogen peroxide at 37° to 44° C. with care taken to avoid containment of the gas generating reaction. The container was sealed and it was placed into the centrifuge. The centrifuge was balanced. The grafts were centrifuged at 2,600 rpm for 15 minutes. The tissue was removed from the centrifuge and the grafts were placed into an ultrasonic cleaner to the ultrasonic cleaner was added a mixture of Allowash™ solution, hydrogen peroxide, and antibiotics and the tissue was sonicated at 37°–44° C. for 1 hour. The tissue was removed from the ultrasonic cleaner. The antibiotic mixture was decanted and the container was filled with fresh hydrogen peroxide. The top was closed and the grafts were sonicated for one hour. After the sonicator was turned off, the grafts were incubated overnight at 37°–44° C. (a minimum of 6 hours). The hydrogen peroxide was decanted and the container was filled with 70% isopropyl alcohol and the grafts were incubated at room temperature for a minimum of 15 minutes. The 70% isopropyl alcohol was decanted and the container was filled with warm (37°–44° C.) sterile water. The grafts were incubated for a minimum of 5 minutes. The sterile water was decanted and the grafts were removed from the container. The tibia head was placed in a sterile container. The container was sealed and placed into the centrifuge. The centrifuge was determined to be balanced. The grafts were centrifuged for 3 minutes to dry and removed any remaining water. The diameter and length of the graft were measured and assigned graft identification numbers. The fashioned graft(s) was placed into the inner package and heat sealed. The fashioned graft(s) were packaged as appropriate for the particular needs of distribution.

Example 5

Process for Cleaning a Proximal Humerus

All soft-tissue and periosteum were removed from the proximal humerus using periosteal elevators and sharp dissection. The humerus was placed securely in Pan-A-Vise™ with the humerus head oriented superiorly or the humerus was held directly on the working surface. The humerus was cut to fashion the humerus head. The humerus head was fashioned into the appropriate sized grafts using a Stryker® saw with single blade assembly. The humerus head was removed from the proximal humerus by cutting the base of the grafts away from the remaining proximal humerus using a Stryker® saw with single blade assembly. The humerus head was cleaned using the pulsatile water apparatus or the grafts were shaken in a container with warm water (37°–44° C.). The humerus head was placed in a sterile container with hydrogen peroxide at 37° to 44° C. with care taken to avoid containment of the gas generating reaction. The container was sealed and it was placed into the centrifuge. The centrifuge was balanced. The grafts were centrifuged at 2,600 rpm for 15 minutes. The tissue was removed from the centrifuge and the grafts was placed into an ultrasonic cleaner to the ultrasonic cleaner was added to a mixture of Allowash™ solution, hydrogen peroxide, and antibiotics and the tissue was sonicated at 37°–44° C. for 1 hour. The tissue was removed from the ultrasonic cleaner. The antibiotic mixture was decanted and the container was filled with fresh hydrogen peroxide. The top was closed and the grafts were sonicated for one hour. After the sonicator was turned off, the grafts were incubated overnight at 37°–44° C. (a minimum of 6 hours). The hydrogen peroxide was decanted and the container was filled with 70% isopropyl alcohol and the grafts were incubated at room temperature for a minimum of 15 minutes. The 70% isopropyl alcohol decanted and the container was filled with warm (37°–44° C.) sterile water. The grafts were incubated for a minimum of 5 minutes. The sterile water was decanted and the grafts were removed from the container. The humerus head was placed in a sterile container. The container was sealed and it was placed into the centrifuge. The centrifuge was determined to be balanced. The grafts were centrifuged for 3 minutes to dry and removed any remaining water. The diameter and length of the graft were measure and assigned graft identification numbers. The fashioned graft(s) were packaged as appropriate for the particular needs of distribution.

While the invention has been described in connection with specific embodiments thereof, it will be understood that it is capable of further modifications and this application is intended to cover any variation, uses, or adaptions of the invention following, in the principle of the invention and including such departures from the present disclosure as came within known or customary practice within the art to which the invention pertains and as may be applied to the essential features hereinbefore set forth as follows in the scope of the appended claims. All references including patents and co-pending patent applications cited herein are hereby incorporated herein by reference in their entirety.

What is claimed:

1. A process for producing a cleaned cut bone graft suitable for transplantation into a human, comprising:
   centrifuging a cut bone graft under conditions effective to remove bone marrow from cancellous bone spaces of said cut bone graft.

2. A process for cleaning a cut bone graft, comprising:
   selecting a substantially intact bone;
   cutting said substantially intact bone into one or more cut bone grafts; and
   centrifuging said cut bone graft under conditions sufficient to remove bone marrow from cancellous bone spaces of said cut bone graft.

3. The process according to any one of claims 1 or 2, further comprising: prior to said step of centrifuging, pre-cleaning said cut bone graft in a pre-cleaning solution to produce a pre-cleaned cut bone graft.

4. The process according to claim 3, farther comprising: after said step of pre-cleaning, cleaning said pre-cleaned cut bone graft in a first cleaning solution to produce a first cleaned bone graft.

5. The process according to claim 4, further comprising: after said step of centrifuging, second cleaning said cut bone graft in a second cleaning solution to produce a second cleaned cut bone graft.

6. The process according to claim 5, further comprising: optionally, after said step of second cleaning first, washing said second cleaned cut bone graft with a first washing solution to produce a first washed cut bone graft.

7. The process according to claim 6, further comprising: optionally, after said step of first washing, second washing said first washed bone graft with a second washing solution to produce a second washed bone graft.

8. The process according to claim 3, wherein said pre-cleaning solution comprises one or more members selected from the group consisting of: water, saline, an alcohol, and hydrogen peroxide.

9. The process according to claim 8, wherein said pre-cleaning solution further comprises one or more members selected from the group consisting of: an antiviral agent, an antibacterial agent, and an antifungal agent.

10. The process according to claim 4, wherein said first cleaning solution comprises one or more members selected from the group consisting of: water alcohol, saline, a decontaminating agent, a permeation enhancer, an amphiphilic component, an organic acid, and a dilute solution of one or more strong acids.

11. The process according to claim 5, wherein said second cleaning solution comprises one or more members selected from the group consisting of: water alcohol, saline, a decontaminating agent, an antiviral agent, a permeation enhancer, an amphiphilic compound, an organic acid, and a dilute solution of one or more strong acids.

12. The process according to claim 4, wherein said pre-cleaning comprises pulsatile lavage or agitation.

13. The process of claim 12, wherein said agitation is performed in a paint can shaker at from 300 to 700 rpm for a time period of at least 5 minutes.

14. The process according to claim 6, wherein said first washing solution comprises a decontaminating agent.

15. The process according to claim 7, further comprising: second centrifuging said second washed bone graft to produce a cleaned bone graft essentially free from bone marrow.

16. The process according to claim 15, further comprising: prior to said step of second centrifuging and after said step of second washing, second incubating said second washed bone graft in a solution comprising water.

17. The process according to claim 5, wherein said step of second cleaning comprises sonication.

18. The process according to claim 6, wherein said step of first washing comprises sonication.

19. The process according to any one of claims 6 or 14, further comprising: after said step of first washing, first incubating said first washed cut bone graft in said first washing solution for a time period of at least 6 hours.

20. The process according to claim 19, wherein said first incubating comprises soaking.

21. The process according to claim 3, further comprising collecting waste solution in a disposable container.

22. The process according to claim 21, further comprising adding at least one strong viral or bacterial inactivator to said waste solution.

23. The process according to any one of claims 10 or 11, wherein said amphiphilic component comprises one or more detergents.

24. The process according to any one of claims 10 or 11, wherein said first or said second cleaning solution comprises: 0.06 wt % polyoxyethylene-4-lauryl ether; 0.02 wt % poly (ethylene glycol)-p-nonyl-phenyl-ether; 0.02 wt % octylphenol-ethyleneoxide, and water.

25. The process according to claim 24, wherein said Allowash™ solution is at a concentration of between 10.0% and 0.1%.

26. The process according to claim 25, wherein Allowash™ solution is at a concentration of 0.1%.

27. The process according to claim 2, further comprising: prior to said step of cutting, removing bone marrow from a luminal space of said substantially intact bone.

28. The process according to claim 23, wherein said amphiphilic component comprises at least one solvent selected from the group consisting of: an anionic detergent, a cationic detergent, and a non-ionic detergent.

29. The process according to any one of claims 10 or 11, wherein said alcohol comprises ethanol.

30. The process according to claim 28, wherein said amphiphilic component comprises at least one solvent selected from the group consisting of: a polyoxyethylene alcohol, a polyethylene glycol p-isooctylphenylether, polyoxyethylene nonylphenol, and a polyoxyethylene sorbitol ester.

31. The process according to claim 29, wherein said second cleaning solution comprises at least one solvent selected from the group consisting of: a polyoxyethylene alcohol, a polyethylene glycol p-isooctylphenylether, polyoxyethylene nonylphenol, and a polyoxyethylene sorbitol ester.

32. The process according to claim 4, wherein said first cleaning solution comprises a 0.01% to 1000.0% concentration of a 100.0% (full strength) detergent solution comprising about 0.066 wt % Brij-35, about 0.02 wt % Nonidet P-40, and about 0.02 wt % Nonoxynol-9, in endotoxin free water.

33. The process according to claim 5, wherein said second cleaning solution comprises about a 0.01% to 1000.0% concentration of a 100% (full strength) detergent solution comprising about 0.066 wt % Brij-35, about 0.02 wt % Nonidet P-40, and about 0.02 wt % Nonoxynol-9, in endotoxin free water.

34. The process according to claim 32, wherein said cleaning solution comprises about 0.1% to 10.0% of said 100.0% detergent solution.

35. The process according to claim 33, wherein said cleaning solution comprises about 0.1% to 10.0% of said 100.0% detergent solution.

36. The process according to claim 34, wherein said cleaning solution comprises about 0.1% to 1.0% of said 100.0% detergent solution.

37. The process according to claim 35, wherein said cleaning solution comprises about 0.1% to 1.0% of said 100.0% detergent solution.

38. The process according to claim 36, wherein said cleaning solution comprises about 0.5% to 1.0% of said 100.0% detergent solution.

39. The process according to claim 37, wherein said cleaning solution comprises about 0.5% to 1.0% of said 100.0% detergent solution.

40. The process according to claim 5, wherein said second cleaning solution comprises a hydrogen peroxide solution.

41. The process according to claim 40, wherein said hydrogen peroxide solution comprises about 5 to 95% ethanol or isopropanol, measured by a volume-to-volume ratio.

42. The process according to claim 41, wherein said hydrogen peroxide solution comprises about 10 to 30% ethanol or isopropanol, measured by a volume-to-volume ratio.

43. The process according to claim 3, wherein said pre-cleaning solution comprises water and at least one detergent selected from the group consisting of: an anionic detergent, a cationic detergent and a non-ionic detergent.

44. The process according to claim 43, wherein said detergent is at a concentration of from about 0.001 to 2.0 wt %.

45. The process according to claim 43, wherein said pre-cleaning solution further comprises ethanol and/or hydrogen peroxide.

46. The process according to claim 43, wherein said pre-cleaning solution comprises at least one non-ionic solvent selected from the group consisting of: a polyoxyethylene alcohol, a polyethylene glycol p-isooctylphenylether, polyoxyethylene nonylphenol, and a polyoxyethylene sorbitol ester.

47. The process according to claim 44, wherein said detergent is at a concentration of from about 0.01 to 0.5 wt %.

48. The process according to any one of claims 1, 2, 16, 17, 20 or 21, wherein said process is carried out within a temperature range of about 20° C. to 65° C.

49. The process according to claim 48, wherein said temperature range is from about 27° C. to 55° C.

50. The process according to claim 49, wherein said temperature range is from about 37° C. to 44° C.

51. The process according to any one of claims 1 or 2, further comprising: monitoring solution exiting said cut bone graft to determine when essentially all of said bone marrow has been removed from said cut bone graft.

52. The process according to claim 51, wherein said monitoring comprises measuring absorbance at a range of from about 410 nm to 700 nm.

53. The process according to claim 52, wherein said monitoring comprises measuring absorbance at 410 nm.

54. The process according to claim 51, wherein said monitoring comprises a visual monitoring of a color of solution exiting said cut bone graft.

55. A bone graft produced by the process recited in claim 1.

56. A bone graft produced by the process recited in claim 2.

57. A process for cleaning a cut bone graft, comprising:
selecting a large, substantially intact bone;
removing excess soft tissue from said substantially intact bone;
cutting said substantially intact bone into one or more cut bone grafts;
incubating said cut bone graft with one or more solutions comprising one or more members selected from the group consisting of water, saline, a detergent, and a decontaminating agent to produce incubated cut bone grafts; and
centrifuging said incubated cut bone grafts under conditions sufficient to remove bone marrow from cancellous bone spaces to produce a cleaned cut bone graft suitable for transplantation into a human.

58. The process according to claim 57, further comprising:
after said step of centrifuging, second incubating said cut bone grafts with one or more solutions comprising one or more members selected from the group consisting of: water, saline, a detergent, and a decontaminating agent, to produce a second incubated cut bone graft; and
second centrifuging said second incubated bone graft under conditions sufficient to remove bone marrow from cancellous bone spaces to produce a cleaned cut bone graft suitable for transplantation into a human.

59. The process according to any one of claims 1, 2, 57 or 58, wherein said centrifuging comprises centrifuging said cut bone graft at 2,000 to 3,000 rpm for 5 to 20 minutes.

60. The process according to claim 59, wherein said centrifuging is carried out at temperatures between 0° C. and 45° C.

61. The process according to any one of claims 57 or 58, wherein said detergent comprises: about a 0.01% to 1000.0% concentration of a 100.0% (full strength) detergent solution comprising about 0.066 wt % Brij-35, about 0.02 wt % Nonidet P-40, and about 0.02 wt % Nonoxynol-9, in endotoxin free water.

62. The process according to claim 61, wherein said detergent comprises about 0.1% to 10.0% of said 100.0% detergent solution.

63. The process according to claim 62, wherein said detergent comprises about 0.1% to 1.0% of said 100.0% detergent solution.

64. The process according to claim 63, wherein said detergent comprises about 0.5% to 1.0% of said 100.0% detergent solution.

65. A process for producing a cleaned cut bone graft suitable for transplantation into a human comprising:
pre-cleaning a cut bone graft with a pre-cleaning solution to produce a pre-cleaned cut bone graft;
incubating said pre-cleaned cut bone graft in a cleaning solution to produce a cleaned cut bone graft; and
centrifuging said cleaned cut bone graft to produce a centrifuged cut bone graft essentially free from bone marrow.

66. The process of claim 2, further comprising:
after said step of centrifuging, incubating said centrifuged cut bone graft in a cleaning solution to produce a cleaned cut bone graft;
washing said cleaned bone graft in a washing solution to produce a washed cut bone graft; and
centrifuging said washed cut bone graft to produce a cut bone graft essentially free from bone marrow.

67. A process for producing a cleaned cut bone graft suitable for transplantation into a human, comprising:
pre-cleaning a cut bone graft with a pre-cleaning solution to produce a pre-cleaned cut bone graft;
cleaning said pre-cleaned cut bone graft with a cleaning solution to produce a cleaned cut bone graft;
centrifuging said cleaned cut bone graft to produce a centrifuged bone graft;
washing said centrifuged bone graft with a washing solution to produce a washed bone graft;
incubating said washed bone graft with water to produce a water washed cut bone graft; and
centrifuging said water washed cut bone graft to produce a cut bone graft essentially free from bone marrow.

* * * * *